United States Patent [19]

Cohen

[11] Patent Number: 5,265,459
[45] Date of Patent: Nov. 30, 1993

[54] SINGLE-ELEMENT THERMAL CONDUCTIVITY DETECTOR

[75] Inventor: Sidney R. Cohen, Derby, Conn.

[73] Assignee: The Perkin Elmer Corporation, Norwalk, Conn.

[21] Appl. No.: 748,588

[22] Filed: Aug. 22, 1991

[51] Int. Cl.⁵ ............................................. G01N 25/18
[52] U.S. Cl. ..................................... 73/25.03; 422/96
[58] Field of Search ............... 73/25.03, 25.25, 31.05, 73/31.06; 422/86

[56] References Cited

U.S. PATENT DOCUMENTS

| | | | |
|---|---|---|---|
| 2,279,231 | 4/1942 | Gier, Jr. | 73/25.03 |
| 2,687,342 | 9/1954 | Strange et al. | 422/96 |
| 2,751,777 | 6/1956 | Cherrier | 73/25.03 |
| 2,876,064 | 3/1959 | Yant et al. | 422/96 |
| 3,305,000 | 2/1967 | Bullen et al. | 73/23.25 |
| 3,519,391 | 7/1970 | Winter et al. | 422/96 |
| 3,864,959 | 2/1975 | MacDonald | 73/25.03 |
| 4,254,654 | 3/1981 | Clouser et al. | 73/25.03 |
| 4,312,213 | 6/1982 | Schlau | 73/25.03 |
| 4,443,793 | 4/1984 | Hall | 73/31.05 |
| 4,854,155 | 8/1989 | Poli | 73/31.05 |

FOREIGN PATENT DOCUMENTS

| | | |
|---|---|---|
| 0021225 | 1/1981 | European Pat. Off. |
| 0281966 | 9/1988 | European Pat. Off. |
| 2193487 | 2/1974 | France |
| 2374639 | 7/1978 | France |

Primary Examiner—Hezron E. Williams
Assistant Examiner—Helen Kwok
Attorney, Agent, or Firm—John R. Wahl; Edwin T. Grimes

[57] ABSTRACT

A Wheatstone bridge type thermal conductivity sample gas detector. A sensing element comprising one arm of the bridge is disposed in a constant temperature oven. A variable resistor, which functions as a reference element, and two fixed resistances comprise the second, third, and fourth arms of the bridge. Carrier gas is circulated around the sensing element and the bridge is balanced by use of the variable resistor. Thereafter, any unbalance of the bridge is caused by sample gas intermingling with the carrier gas, thereby providing a signal representation of the sample.

5 Claims, 1 Drawing Sheet

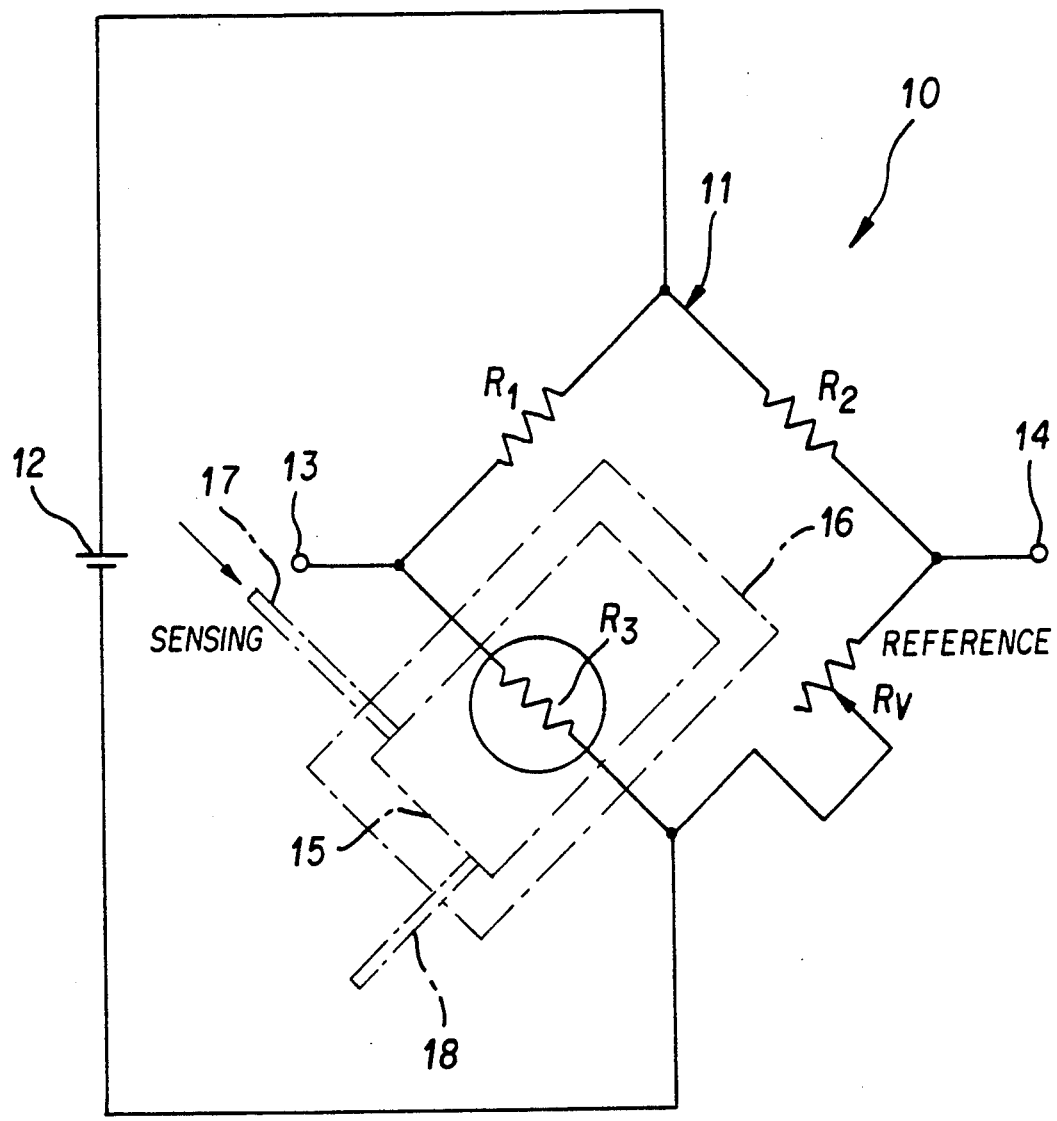

SINGLE-ELEMENT THERMAL CONDUCTIVITY DETECTOR

BACKGROUND OF THE INVENTION

Conventional thermal conductivity detectors used in detecting sample gas normally employ two sensors in a bridge configuration. Both sensors are enclosed in a constant temperature oven. The sensors are of the type, e.g., thermistors or hot wires, whose resistances vary as a function of their temperatures. The two sensors ideally are matched identically at the factory to have identical electrical characteristic.

These detectors operate in the following manner: Carrier gas (e.g., helium, argon, etc.) flows through individual cells containing the thermistor (or hot wires) at some constant rate. A bridge balance is established under these conditions. Next, the sample to be analyzed is introduced into the carrier gas flowing through one thermistor identified as the "sample" or "sensor" side of the bridge. No sample is introduced into the carrier gas flow through the other thermistor identified as the "reference" side of the bridge. The sample is in gaseous form, usually the evolved product(s) of combustion of a solid sample. The mixture of the sample gas (or gases) has a thermal conductivity higher (or lower) than the carrier. This change in thermal conductivity of the gas mixture passing over the "sample" thermistor causes the thermistor temperature to change by virtue of heat loss (or gain), thereby changing its resistance. Since the "reference" thermistor resistance remains constant, the bridge becomes unbalanced, causing a voltage signal to be generated. This signal may be amplified by appropriate electronic circuitry. Finally, samples whose constituents and their weight percentages are known are used to calibrate the apparatus.

Matching sensors to have identical electrical characteristic is costly and almost never perfectly achievable. Since these sensors must be balanced with respect to several parameters, including ohmic resistance at room and operating temperatures, offset, i.e., differences in resistance at operating temperatures and drift, i.e., variation of resistance with time, the testing required to insure the required balance imposes significant costs, particularly in those cases such as drift, where the defect cannot be detected until the detector is completely assembled.

The foregoing described problems can be virtually eliminated by using only one sensor and substituting a variable resistance for the previously required sensor.

In carrying out the present invention, an arm of a Wheatstone bridge circuit carrying the sensor is the only part of the bridge circuit enclosed in a constant temperature oven. The reference arm, i.e., the one containing the variable resistance, is located outside the oven. In operation, a carrier gas is caused to flow over the sensor in the oven. The variable resistance is changed until the voltage output from the bridge is zero or some other acceptable value. Then, a sample gas is introduced and intermingled with the carrier gas. The change in thermal conductivity of the mixture from the carrier gas is representative of the sample. This unbalances the bridge so that the bridge output signal is indicative of the sample.

DESCRIPTION OF THE DRAWING

The Figure is a schematic representation of the present invention.

DESCRIPTION

Referring more particularly to the Figure, there is shown the single-element thermal conductivity detector 10 of the present invention. It essentially comprises a Wheatstone bridge arrangement 11. The Wheatstone bridge comprises arms containing resistance $R_1$ and $R_2$ and of equal value. These resistances are joined at a point connected to the positive side of a DC power source, such as battery 12 or a regulated DC supply. The remaining two arms of the bridge circuit 11 comprise a variable resistance $R_v$ and a sensor $R_s$. In a practical embodiment, sensor $R_s$ comprises a thermistor but may comprise any equivalent sensor whose resistance varies with temperature. The juncture of variable resistance $R_v$ and sensor $R_s$ is connected to the negative side of DC source 12. The juncture of resistance $R_1$ and sensor $R_s$ is connected to output terminal 13, while the juncture of resistance $R_2$ and variable resistance $R_v$ is connected to output terminal 14. Output terminals 13 and 14 may be connected to a voltmeter or any similar detector for determining the output voltage of the system.

A detector cell 15 encloses sensor $R_s$. Detector cell 15 is enclosed within an oven 16. Detector cell 15, which encloses a relatively small volume, has an input tube 17 and an output tube 18 for carrying gas into and out of the detector cell. In helium, the thermistor resistance would be approximately 3000–3500 ohms at 82°. In argon, the thermistor resistance would be approximately 1500 ohms at 82°. Resistances $R_1$ and $R_2$ would, for example, be 3600 ohms.

The principle of the present invention is based on thermal conductivity of gases. Since gases have different thermal conductivities, accurate measurement of the thermal conductivity of a gas may be used to identify the sample.

In operation, a carrier gas is introduced into detector cells 15, where it bathes the sensor $R_s$, which, as aforesaid, may be a thermistor. Since the oven 16 is maintained at a constant temperature, e.g., 82° C., the resistance of the thermistor soon reaches a stable condition. At this point, resistance $R_v$ is varied until the bridge is balanced, i.e., until the potential at output terminals 13 and 14 is zero or some value. When the bridge has reached equilibrium, the sample gas is introduced, along with the carrier gas, into the detector cell 15. This unbalances the bridge and the degree of unbalance, caused by the change in thermal conductivity, is indicated by the signal at output terminals 13 and 14. This signal is representative of the sample gas and may be input into an indicator for sample gas identification.

The advantages of the foregoing described single-element thermal conductivity detector are:

1. Since only one thermistor is employed, significant economies are achieved in parts costs, parts testing (virtually eliminated), detector plumbing, general manufacturing costs, and final testing of the complete instrument. The resultant simplicity and reduced parts count increase reliability of the instrument.

2. Since the thermistor vendor no longer is required to match pairs, the rejection rate is reduced with a concomitant reduction in cost.

3. The external variable resistor provides rapid and easy coarse bridge balancing with any thermistor (within the resistance specifications. In this case, it is 100,000 ohms ±15% at 25° C.). Additional conventional external circuitry may be required to provide fine balancing.

What is claimed is:

1. A thermal conductivity detector comprising:

first, second, third, and fourth arms, one end of each of said first and second arms joined at a first juncture, one end of each of said third and fourth arms joined at a second juncture, the other ends of said first and second arms joined at the other ends of said third and fourth arms at third and fourth junctures, respectively, said first and second arms containing resistances of equal value, said third arm containing a temperature responsive resistance, said fourth arm containing a variable resistance, means for applying a voltage across said first and second junctures, output terminal means connected to said third and fourth juncture, and a detector cell enclosing said temperature responsive resistance and a constant temperature oven enclosing said detector cell for maintaining gas in said detector cell at a predetermined temperature, said variable resistance being disposed outside said constant temperature oven, whereby a signal on said output terminal means is representative of the thermal conductivity of said gas.

2. A thermal conductivity detector according to claim 1, wherein said detector cell further comprises ingress and egress tubes for circulating gas into and out of said detector cell for bathing said heat responsive resistance with said gas.

3. A thermal conductivity detector, according to claim 2, wherein said resistance in said fourth arm may be varied to cause the signal on said output terminals to be zero when a carrier gas is circulated through said detector cell whereby, when a sample gas is intermingled with said carrier gas, the thermal conductivity of the gases causes a signal to appear on said output terminals which is an indication of the identity of the sample gas.

4. A thermal conductivity detector according to claim 3, wherein said heat responsive resistance is a thermistor.

5. A thermal conductivity detector according to claim 3, wherein said heat responsive resistance is a hot wire.

* * * * *